United States Patent
Schloemer et al.

(10) Patent No.: US 6,531,611 B2
(45) Date of Patent: Mar. 11, 2003

(54) PROCESS FOR MAKING TAXANE DERIVATIVES

(75) Inventors: George Schloemer, Longmont, CO (US); Yung-Fa Chen, Tainan (TW); Chien Hsin Lin, Taipei (TW); Wlodzimierz Daniewski, Ul. Zamlany (PL)

(73) Assignee: Scinopharm Taiwan, Ltd., Tainan (TW)

( * ) Notice: Subject to any disclaimer, the term of this patent is extended or adjusted under 35 U.S.C. 154(b) by 95 days.

(21) Appl. No.: 09/815,517

(22) Filed: Mar. 23, 2001

(65) Prior Publication Data

US 2002/0137955 A1 Sep. 26, 2002

(51) Int. Cl.⁷ ..................... C07D 263/06; C07D 305/14
(52) U.S. Cl. .................. 548/215; 549/510; 549/511
(58) Field of Search .......................... 548/215; 549/510, 549/511

(56) References Cited

U.S. PATENT DOCUMENTS 5,470,866 A * 11/1995 Kingston et al. ............ 514/376
5,476,954 A * 12/1995 Bourzat et al. ............. 549/510

* cited by examiner

*Primary Examiner*—Ba K. Trinh
(74) *Attorney, Agent, or Firm*—Cohen, Pontani, Lieberman & Pavane

(57) ABSTRACT

The present invention provides a novel semi-synthetic method of producing a variety of novel taxane derivatives. The method involves the reaction of a phenylisoserine derivative with a suitably blocked Baccatin III derivative to produce a taxane substrate that may be further modified to form Pactitaxel and other potentially useful taxane derivatives.

15 Claims, No Drawings

PROCESS FOR MAKING TAXANE DERIVATIVES

BACKGROUND OF THE INVENTION

1. Field of the Invention

The present invention relates to a novel semi-synthetic method of producing the cancer drug, Paclitaxel. The method employs a unique method of obtaining unsaturated derivatives by the use of activated oxazoles which can subsequently be hydrolyzed to taxane derivatives useful in an oxidative-rearrangement procedure producing Paclitaxel. The method has the potential to be useful in the synthesis of a variety of novel taxane derivatives.

2. Description of the Related Art

The semi-synthesis of taxanes from 10-deacetyl baccatin III ("10-DAB III") has been actively pursued for several years. The first synthesis was demonstrated by Greene et. al.[1] but was inefficient in that a large excess of the costly side-chain was used, low yields were obtained and epimerization of the 2'-position was a problem. Holton, et. al.[2] demonstrated a more efficient synthesis utilizing cyclic amide derivatives. This synthesis is being used commercially by Bristol-Myers Squibb. Rhone-Poulenc Rorer showed an efficient synthesis of taxotere and Paclitaxel employing specific cyclic acetal derivatives[3]. Finally, Bristol-Myers demonstrated an efficient synthesis using oxazoline derivatives[4]. A number of other syntheses have been described but are of lesser value. While a number of the above routes are quite efficient, they do not allow for the ready formation of other taxane derivatives from an advanced common intermediate as is the case in our synthesis. The specific side-chain amide must be formed at the start of the synthesis.

The present inventors sought a method that would produce a variety of useful taxane derivatives from a common intermediate. Our initial interest was sparked by a method published by Kingston et.al.[5]. It was thought that if we could discover a novel, efficient method of producing these intermediates, we would be able to develop a commercial synthesis capable of producing a number of valuable taxanes. This present invention accomplishes our goal. Likewise, we have found the Kingston conditions to be rather ineffective and we have had to considerably modify them to obtain the desired results.

SUMMARY OF THE INVENTION

An efficient method of production of Paclitaxel has been invented. The method involves the production of an unique phenylisoserine derivative which is then reacted with a suitably blocked Baccatin III derivative to produce a taxane substrate which may be elaborated into Paclitaxel and other potentially useful taxane derivatives. The invention is disclosed in greater detail as follows.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Initially an α, β-unsaturated amide of 2R,3S-phenylisoserine is produced by the reaction of 2R,3S-phenylisoserine HCl (1) with methanol and thionyl chloride to esterify the acid group and form the methyl ester. This compound is subsequently reacted with α-methylcinnamoyl chloride under basic to neutral conditions to produce the amide (2) as a crystalline substance. Compound 2 is cyclized with an activated benzaldehyde dimethyl acetal under acidic catalysis to form compound 3. A suitable solvent is toluene under atmospheric reflux or under reduced pressure reflux. However, other non-reactive solvents capable of methanol removal can also be used. An activated benzaldehyde is defined as containing at least one electron releasing methoxy group on the ring and is necessary to facilitate hydrolysis in the next step. The activated grouping must also be able to provide for the formation of the side-chain acid and also for the hydrolysis after coupling to the blocked baccatin derivative without significant decomposition of the taxane structure. We have discovered that benzaldehydes containing an alkyl ether group in the 4-position are suitable but even better are benzaldehydes containing two alkyl ether groups. The methoxy group is preferred and 3,4-dimethoxybenzaldehyde has proven to be the most suitable activated benzaldehyde. Compound 3 is hydrolyzed with base and acidified to produce the carboxylic acid (4) ready for coupling. The conditions of this hydrolysis and acidification step must be selected to avoid epimerization of the 2-position in the phenyl isoserine moiety or, in the case of the acid, to avoid cleavage of the sensitive oxazole intermediate. Bases such as metal hydroxides are preferable and lithium hydroxide is preferred. Suitable solvents are alcohols and THF. The acidification can be preformed using a variety of acids but hydrochloric acid to pH approximately 2 or citric acid are preferred.

10-Deacetyl baccatin III ("10-DAB") is obtained from *Taxus baccata* needles as a renewable resource. The 7-position of this compound is protected by a protecting group such as a silyl ether. The preferred protecting group is a triethylsilyl ether. The triethylsilyl ether can be attached by several known methods such as pyridineTESCl or DMF/imidazole/TESCl. 7-Triethylsilyl-10-deacetylbaccatin III (7-TES-10-DAB III) is then converted to 7-TESbaccatin III (5) by acetylation of the 10-hydroxyl. This acetylation can be accomplished in pyridine with acetyl chloride or by by deprotonation with alkyl lithium and acetylation with acetic anhydride. Compound 5 is now suitable for coupling with the acid derivative previous mentioned (4).

The coupling of 5 and 4 to produce compound 6 can readily be accomplished employing dicyclohexylcarbodiimide with DMAP. Suitable solvents are toluene and ethyl acetate or similar organic solvents. Suitable temperatures are from 0° C. to reflux however 25–40° C. is preferred. Compound 6 can readily be isolated as a solid substance. The two blocking groups must now be removed under acidic conditions. The triethylsilyl group can readily be removed but the oxazole group requires activation for removal. Without activating groups, mainly decomposition is observed. Suitable solvents for this reaction are alcohol or THF and strong acid catalysts such as gaseous hydrogen chloride, aqueous HCl or trifluoroacetic acid is employed. Suitable temperatures for the reaction are between 0° C. to reflux but 0–40° C. is preferred. Complete cleavage of the blocking groups result in formation of compound 7. The 2'-position is selectively benzoylated using a variety of conditions. We have found that benzoyl chloride/triethylamine/sodium hydrogen carbonate in methylene chloride is particularly suitable for this conversion. Other conditions include DCC/benzoic acid in toluene. Compound 8 is formed. The synthesis is completed by the oxidative cleavage of the olefin with ozone to produce compound 9 which is rearranged further to Paclitaxel with conditions similar to those indicated by Kingston. Purification of the resulting Paclitaxel can be accomplished readily by chromatographic means and crystallization.

The following summarizes the general reaction steps discussed above.

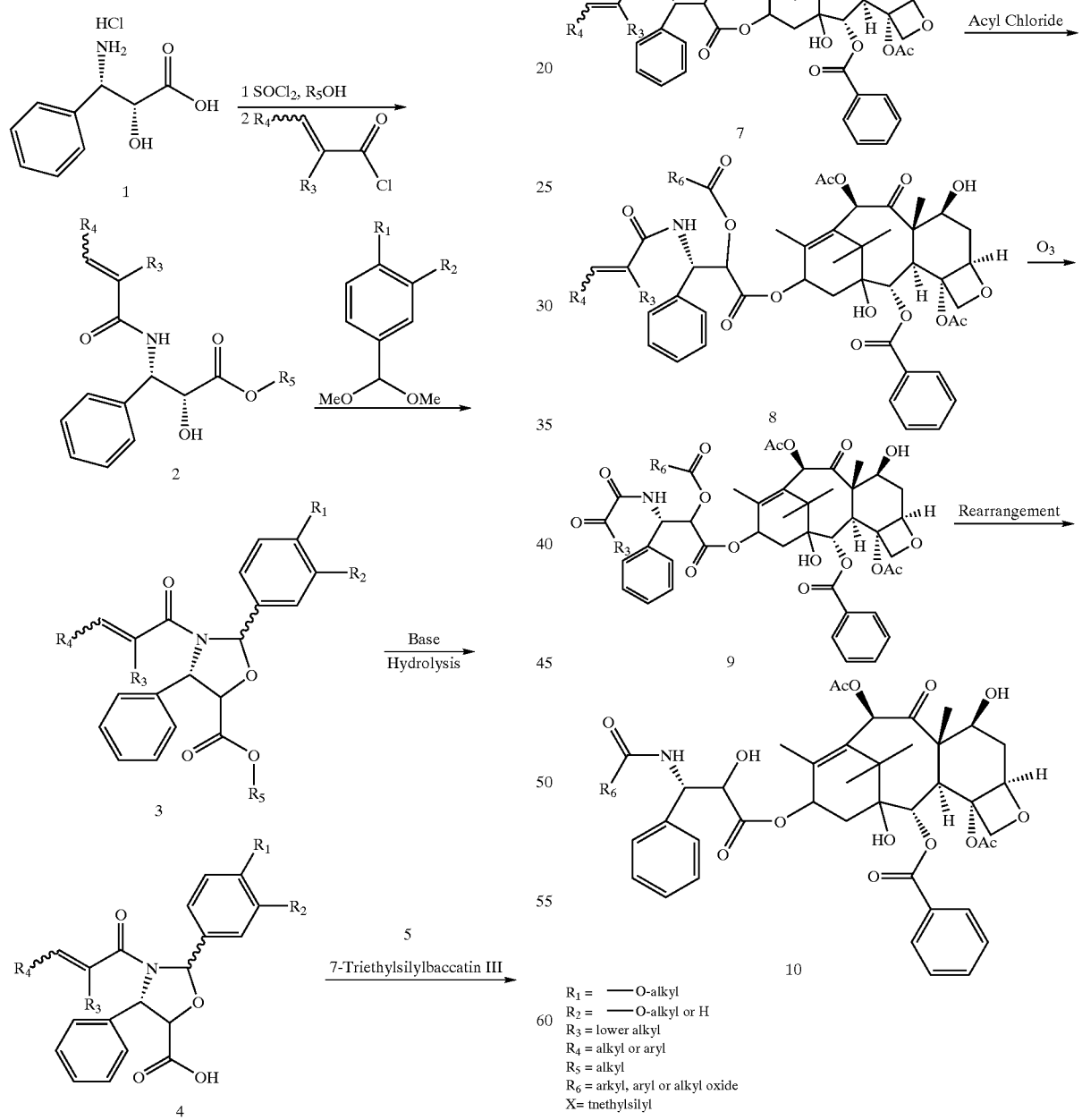

References
1. J. N. Denis, A. E. Greene, D. Guenard, F. Gueritte-Vogelein, L. Mangantal, P. Potier, J. Amer. Chem. Soc., 1988, 110, 5917.
2. R. A. Holton, EPA 400971, 1990.
3. Rhone-Poulenc Rorer, U.S. Pat. No. 5,476,954; WO 94/07878; WO 94/07879.
4. Bristol-Myers Squibb, EPA 0735036 A1, 1996.
5. Kingston, Molinero, Gunatilaka, U.S. Pat. No. 5,470,866, 1995.

EXAMPLE 1

Synthesis of 7-Triethylsilyl-baccatin III (Compound 5)

50 gm (7.44 mmole) of 7-TES-10-DAB III was dissolve in 700 ml of THF and cooled to −55° C. 80 ml of 1.1 M BuLi in hexane was added slowly and the mixture was stirred for 60 min at −55° C. Acetic anhydride (22.5 gm) was added slowly and the mixture was stirred for 60 min at −55° C. After removing cool bath and warming to room temperature, extraction by adding 450 ml of water and 1000 ml of ethyl acetate to the reaction mixture gave organic solution. The solution was dried over magnesium sulfate. Evaporating the solvent till 70 ml of the solution is left, and adding 150 mL of heptane gave a precipitate. Filtration gave 7-triethylsilyl baccatin III 46.5 g (87%).
$^1$H NMR (400 MHz, $CD_3COCD_3$) δ: 0.64 (q, J=7.9 Hz, 6H), 0.97 (t, J=7.9 Hz, 9H), 1.09 (s, 3H), 1.21 (s, 3H), 1.69 (s, 3H), 1.78 (m, 1H), 2.14 (s, 3H), 2.19 (d, J=1.1 Hz, 3H), 2.28 (s, 3H), 2.35 (m, 1H), 2.48 (m, 2H), 3.55 (s, 1H), 3.95 (d, J=7 Hz, 1 H), 4.17 (s, 2H), 4.53 (t, J=7.0 Hz, 1H), 4.70 (d, J=4.6 Hz, 1H), 4.89–5.02 (m, 2H), 5.68 (d, J=7.0 Hz, 1H), 6.53 (s, 1H), 7.56 (m, 2H), 7.65 (m, 1H), 8.12 (m, 2H).
$^{13}$C NMR (100 MHz, $CD_3COCD_3$) δ: 5.5, 6.7, 10.0, 14.9, 20.4, 22.2, 26.6, 37.7, 43.2, 47.6, 58.7, 67.4, 72.9, 75.3, 76.2, 76.3, 78.0, 80.7, 84.2, 128.9, 130.3, 131.0, 132.5, 133.5, 145.6, 166.1, 169.2, 170.4, 202.4.

EXAMPLE 2

Synthesis of Methyl (2R, 3S) 2-hydroxy-3-(2'-methyl-3'-phenyl-prop-2'-enoylamino)-3-phenyl-propionate (Compound 2)

α-methylcinnamic acid (45 g) and thionyl chloride (50 g) was stirred at 20–30° C. After 5 min, 0.3 ml of DMF was added and kept stirring at 20–30° C. for 1 hour to give crude of α-methylcinnamoyl chloride (solution A)

50 g of (2R,3S)-Phenylisoserine·HCl was dissolved in 750 mL of MeOH and then the mixture was cooled to 0–5° C. Keeping the reaction at 0–5° C., 82.5 g of thionyl chloride was slowly added to the reaction mixture. Afterwards the reaction was stirred for 1 hr at 0–5° C. (solution B). 1 L of Ethyl acetate and 900 mL of $H_2O$ was added to solution B and the acidity of this mixture was adjusted to pH 8–9 by adding 3N NaOH. Solution A (α-methylcinnamoyl chloride) with 250 ml EA dilution was added to solution B with rapid stirring and the temperature was kept at 0–5° C., during which the pH was adjusted between 8–9 by adding 3N NaOH. After stirring for another 1 hour, the reaction mixture was extracted with ethyl acetate, dried over 35 g of $MgSO_4$, removed solvent under reduced pressure to give 53 g of Compound 2 (93%).
$^1$H NMR (400 MHz, $CDCl_3$) δ: 2.10 (s, 3H), 3.04 (br, 1H), 3.83 (s, 3H), 4.60 (s, 1H), 5.64 (d, J=12 Hz, 1H), 6.82 (d, J=8 Hz, 1H), 7.26–7.45 (m, 10H).

EXAMPLE 3

Synthesis of Methyl (2R,3S) 2-hydroxy-3-(2'-methyl-prop-2'-enoylamino)-3-phenyl-propionate The procedure is similar to the procedure for synthesis of methyl (2R,3S) 2-hydroxy-3-(2'-methyl-3'-phenyl-prop-2'-enoylamino)-3-phenyl-propionate but using methacrylic acid instead of α-methylcinnamic acid.
$^1$H NMR (400 MHz, $CDCl_3$) δ: 1.95 (s, 3H), 3.18 (d, J=3.2 Hz 1H), 3.83 (s, 3H), 4.55 (s, 1H), 5.34 (s, 1H), 5.56 (d, J=8 Hz), 5.69 (s, 1H), 6.60 (d, J=8 Hz, 1H), 7.26–7.39 (m, 5H).

EXAMPLE 4

Synthesis of Methyl (4S,5R)-N-(α-methylcinnamoyl)-2-(3',4'-dimethoxyphenyl)-4-phenyl-5-oxazolidine carboxylate (Compound 3)

A reaction flask containing 11.76 g of 3,4-dimethoxybenzaldehyde, 0.13 g of pTSA, 50 mL of toluene and 9.29 g of trimethylorthoformate was heated to reflux for 30 min. The solvent was removed from the reaction mixture under reduced pressure (50° C., 40 mmHg) for 1 hour till 50 ml of solvent was removed. Afterwards toluene (10 mL) was added to the mixture and the mixture was further distilled under reduced pressure (50° C., 40 mmHg) for 1 hour till 20 ml of solvent was removed. 20 g of Compound 2, 0.56 g pTSA and 120 mL of toluene was added to the reaction mixture. The reaction mixture was then heated to reflux for 1 hour and then the reaction mixture was cooled down to 30–40° C. Washing the mixture with 30 mL of saturated $NaHCO_3$, removing the water layer and removing the organic solvent under reduced pressure gave oily residue. After ethyl acetate (60 mL) was added was added to the oily residue to dissolve the mixture, 420 mL of hexane was added to form a precipitate. After filtration and drying, 25.3 g of Compound 3 was obtained. NMR spectra for mixture of two diastereomers:
$^1$H NMR (400 MHz, $CD_3COCD_3$) δ1.31 (s, 3H; minor), 1.90 (s, 3H; major), 3.63 (s, 3H; major), 3.70 (s, 3H; minor), 3.76 (s, 3H; minor), 3.83 (s, 3H; major), 3.84 (s, 3H; minor), 3.87 (s, 3H; major), 4.75 (d, J=6.0 Hz; minor), 5.07 (d, J=1.4 Hz, 1H; major), 5.67 (d, J=6.0 Hz, 1H; minor), 5.71 (s, 1H; major), 6.42 (s, 1H; major), 6.67 (s, 1H; major), 6.73 (s, 1H; minor), 6.94–7.48 (m, 13H; mix). $^{13}$C NMR (100 MHz, $CD_3COCD_3$ for major) δ15.2, 52.4, 55.4, 55.6, 64.3, 81.9, 91.6, 111.4, 111.6, 120.9, 127.7, 127.9, 128.2, 128.6, 128.9, 129.3, 131.0, 131.2, 133.9, 136.0, 140.4, 149.6, 150.3, 170.8, 173.5.
$^{13}$C NMR (100 MHz, $CDCl_3$ for minor) δ14.3, 52.4, 55.9, 56.1, 64.8, 83.4, 93.3, 111.1, 111.4, 120.5, 126.9, 127.7, 128.2, 128.3, 129.0, 129.0, 130.9, 131.8, 135.4, 135.7, 139.3, 149.3, 150.1, 169.4, 172.1.

EXAMPLE 5

Synthesis of Methyl (4S,5R)-N-(α-methyleinnamoyl)- 2-(4'-methoxyphenyl)-4-phenyl-5-oxazolidine carboxylate The procedure is similar to the procedure for synthesis of methyl (4S,5R)-N-(α-methylcinnamoyl)-2-(3',4'-dimethoxyphenyl)-4-phenyl-5-oxazolidine carboxylate but using 4-methoxybenzaldehyde instead of 3,4-di methoxy-benzaldehyde.
$^1$H NMR (500 MHz, $CDCl_3$) δ: 1.88 (s, 3H), 3.82 (s, 3H), 3.85 (s, 3H), 4.90 (d, J=2.2 Hz, 1H), 5.56 (d, J=1.9 Hz, 1H), 6.40 (d, J=1.4 Hz, 1H), 6.81 (s, 1H), 6.88 (m, 2H), 6.95 (m, 2H), 7.19–7.45 (m, 10 H).

$^{13}$C NMR (125 MHz, CDCl$_3$) δ: 15.4, 52.7, 55.3, 64.4, 81.9, 91.3, 113.7, 127.3, 127.6, 128.1, 128.2, 128.7, 129.0, 123.0, 131.3, 133.1, 135.4, 139.2, 160.0, 170.5.

EXAMPLE 6

Synthesis of (4S,5R)-N-(α-methylcinnamoyl)-2-(3', 4'-dimethoxyphenyl)- 4-phenyl-5-oxazolidine carboxylic acid (Compound 4)

Compound 3 (25 g) in 125 ml of THF was added with 63 ml of 1N LiOH at room temperature. After 30 minutes, the mixture was adjusted to a pH of 2 by adding 1N HCl. After separation of the aqueous part, the organic part was washed with brine and dried over MgSO$_4$. Removing the solvent under reduced pressure gave quantitatively Compound 4.
$^1$H NMR (400 MHz, CD$_3$COCD$_3$) δ: major 1.87 (s, 3H), 3.70 (s, 3H), 3.88 (s, 3H)5.02 (s, 1H), 5.71 (s, 1H), 6.42 (s, 1H), 6.82–7.63 (m, 14H); minor 1.28 (s, 3H), 3.73 (s, 3H), 3.82 (s, 3H), 4.71 (d, J=7.2 Hz, 1H), 5.58 (d, J=7.2 Hz, 1H), 6.64 (s, 1H), 6.92–7.54 (m, 14H).

EXAMPLE 7

Synthesis of 7-Triethylsilyl-baccatin III-13-O-ester with (4S,5R)-N-(α-methylcinnamoyl)-2-(3',4'-dimethoxyphenyl)- 4-phenyl-5-oxazolidine carboxylic acid (Compound 6)

Compound 4 from the above procedure was mixed with 25 g of 7-TES-baccatin III, 12.5 g of dicyclohexylcarbodiimide (DCC), 0.9 g of 4-dimethylaminopyridine (DMAP) and 300 mL of toluene and the mixture was stirred at room temperature for 1 h. To the reaction mixture, 50 mL of 1N HCl was added and stirred for 30 minutes to produce precipitation. Filtering the solid and separating the aqueous part gave crude product in toluene. Washing the crude product with saturated NaHCO$_3$ and brine and removing the solvent under reduced pressure provided dry crude Compound 6.
$^1$H NMR (400 MHz, CDCl$_3$) δ: 0.59 (q, J=8.2 Hz, 6H), 0.94 (t, J=8.0 Hz, 9H), 1.25 (s, 3H), 1.26 (s, 3H), 1.70 (s, 3H), 1.86–1.98 (m, 1H), 1.90 (s, 3H), 2.07 (s, 3H), 2.14 (s, 3H), 2.17–2.21 (m, 1H), 2.21 (s, 3H), 2.21–2.37 (m, 1H), 2.47–2.55 (m, 1H), 3.73 (s, 3H), 3.86 (d, J=6.9 Hz, 1H), 3.93 (s, 3H), 4.15 (d, J=8.3 Hz, 1H), 4.29 (d, J=8.4 Hz, 1H), 4.50 (dd, J=10.2, 6.8 Hz, 1H), 4.90 (d, J=9.5 Hz, 1H), 5.01 (s, 1H), 5.70 (d, J=7.1 Hz, 1H), 5.75 (s, 1H), 6.34 (t, J=8.8 Hz, 1H), 6.42 (s, 1H), 6.49 (s, 1H), 6.81 (s, 1H), 6.88 (d, J=8.4 Hz, 1H), 6.98 (d, J=7.0 Hz, 1H), 7.03 (s, 1H), 7.10 (d, J=7.4 Hz, 1H), 7.15–7.52 (m, 12H), 7.63 (t, J=7.5 Hz, 1H), 8.08 (d, J=7.6 Hz, 2H).

EXAMPLE 8

Synthesis of 7-Triethylsilyl-baccatin III-13-O-ester with (4S,5R)-N-(α-methylcinnamoyl)-2-(4'-methoxyphenyl)- 4-phenyl-5-oxazolidine carboxylic acid The procedure is similar to the procedure for synthesis of 7-triethylsilyl-baccatin III -13-O-ester with (4S,5R)-N-(α-methylcinnamoyl)-2-(4'-methoxyphenyl)-4-phenyl-5-oxazolidine carboxylic acid but using 4-methoxybenzaldehyde instead of 3,4-dimethoxybenzaldehyde.
$^1$H NMR (500 MHz, CDCl$_3$) δ0.58 (q, J=8.0 Hz, 6H), 0.92 (t, J=8.0 Hz, 9H), 1.23 (s, 3H), 1.24 (s, 3H), 1.59 (s, 1H), 1.68 (s, 3H), 1.73 (s, 1H), 1.85–1.92 (m, 1H), 1.89 (s, 3H), 2.05 (s, 3H), 2.12 (d, J=1.0 Hz, 3H), 2.19 (s, 3H), 2.24–2.30 (m, 2H), 2.35 (s, 1H), 2.51 (ddd, J=14.4, 9.7, 6.7 Hz, 1H), 3.82–3.86 (m, 1H), 3.84 (s, 3H), 4.13 (d, J=8.3 Hz, 1H), 4.27 (d, J=8.3 Hz, 1H), 4.48 (dd, J=10.5, 6.7 Hz, 1H), 4.89 (dd, J=9.6, 1.5 Hz, 1H), 4.91 (d, J=1.8 Hz, 1H), 5.67 (s, 1H), 5.68 (d, J=5.2 Hz, 1H), 6.31 (td, J=9.1, 1.2 Hz, 1H), 6.41 (d, J=0.8 Hz, 1H), 6.47 (s, 1H), 6.82 (s, 1H), 6.90–6.96 (m, 4H), 7.44–7.49 (m, 4H), 7.60 (tt, J=7.4, 1.1 Hz, 1H), 8.04–8.08 (m, 2H).
$^{13}$C NMR (125 MHz, CDCl$_3$) δ5.3, 6.7, 10.0, 14.6, 15.4, 20.8, 21.0, 21.4, 22.0, 26.6, 35.4, 37.2, 43.3, 48.8, 55.3, 58.5, 71.6, 72.2, 74.9, 75.0, 76.5, 79.0, 80.9, 84.2, 113.9, 127.5, 127.6, 128.2, 128.3, 128.6, 128.8, 128.8, 129.0, 129.2, 129.8, 130.1, 131.6, 133.0, 133.7, 134.1, 135.3, 139.3, 139.7, 160.1, 167.1, 169.1, 169.9, 167.0, 201.7.

EXAMPLE 9

Synthesis of 7-Triethylsilyl-baccatin III-13-O-ester with (4S,5R)-N-(2'-methyl-but-2'-(E)-enoyl)-2-(3',4'-dimnethoxyphenyl)-4-phenyl-5-oxazolidine carboxylic acid The procedure is similar to the procedure for synthesis of 7-triethylsilyl-baccatin III-13-O-ester with (4S,5R)-N-(α-methylcinnamoyl)-2-(4'-methoxyphenyl)-4-phenyl-5-oxazolidine carboxylic acid but using tiglic acid instead of α-methylcinnamic acid.
$^1$H NMR (400 MHz, CD$_3$COCD$_3$) δ: 0.65 (q, J=7.5 Hz, 6H), 0.98 (t, J=7.9 Hz, 9H), 1.26 (s, 3H), 1.29 (s, 3H), 1.53 (d, J=6.4 Hz, 3H), 1.66 (s, 3H), 1.71 (s, 3H), 1.75–1.85 (m, 1H), 2.16–2.27 (m, 1H), 2.18 (s, 3H), 2.20 (s, 3H), 2.26 (s, 3H), 2.41–2.60 (m, 2H), 3.71 (s, 3H), 3.85 (s, 3H), 3.90–3.96 (m, 2H), 4.17 (s, 2H), 4.60 (dd, J=10.1, 6.7 Hz, 1H), 4.95 (d, J=8.9 Hz, 1H), 5.20 (s, 1H), 5.52 (d, J=5.8 Hz, 1H), 5.76 (d, J=6.8 Hz, 1H), 6.39 (t, J=8.4 Hz, 1H), 6.55 (s, 1H), 6.70 (s, 1H), 6.97 (s, 1H), 6.99 (s, 1H), 7.09 (s, 1H), 7.10 (s, 1H), 7.30–7.72 (m, 8H), 8.10 (d, J=7.4 Hz, 2H).
$^{13}$C NMR (100 MHz, CD$_3$COCD$_3$) δ: 5.4, 6.6, 10.0, 12.6, 13.1, 14.7, 20.3, 21.2, 21.9, 26.4, 36.5, 37.7, 43.8, 47.2, 55.4, 55.6, 58.8, 64.3, 71.8, 72.9, 75.2, 75.4, 76.3, 78.0, 81.0, 82.2, 84.1, 92.8, 111.4, 111.6, 120.4, 127.8, 128.2, 128.3, 128.7, 128.9, 129.0, 130.3, 130.7, 131.2, 133.2, 133.6, 134.8, 139.8, 140.6, 149.7, 150.3, 166.0, 169.2, 170.7, 170.8, 173.6, 201.7.

EXAMPLE 10

Synthesis of 5β, 20-epoxy-1,2α,4,7β,10β,13α-hexahydroxytax-11-en-9-one 4,10-diacetate 2-benzoate 13-ester with (2R,3S)-N- α-methylcinnamoyl-3-phenylisoserine (Compound 7)

Compound 6 from the above procedure was mixed with 85 ml of THF at ice temperature. A pre-cooled solution of 12N HCl (50 mL) and THF (90 mL) was added into the mixture. After stirring for 4 h at ice temperature, 1.3 L of ethyl acetate and 500 mL of water was added to quench the reaction and the aqueous part was separated. The organic solution was washed with saturated NaHCO$_3$ and brine, dried over MgSO$_4$ and removed the solvent under reduced pressure to give crude Compound 7.
$^1$H NMR (400 MHz, CDCl$_3$) δ: 1.17 (s, 3H), 1.28 (s, 3H), 1.70 (s, 3H), 1.72–1.95 (m, 1H), 1.83 (s, 3H), 2.09 (d, J=1.2 Hz, 3H), 2.11–2.18 (m, 1H), 2.26 (s, 3H), 2.27–2.36 (m, 1H), 2.40 (s, 3H), 2.52–2.58 (m, 1H), 3.82 (d, J=6.8 Hz, 1H), 3.98 (d, J=10.4 Hz, 1H), 4.21 (d, J=8 Hz, 1H), 4.32 (d, J=8.4 Hz, 1H), 4.43 (dd, J=10.8, 6.4 Hz, 1H), 4.78 (d, J=2.8 Hz, 1H), 4.96 (dd, J=9.2, 1.6 Hz, 1H), 5.71 (t, J=6.8 Hz, 2H), 6.27 (t, J=8.8 Hz, 1H), 6.30 (s, 1H), 6.76 (d, J=8.8 Hz, 1H), 7.23–7.64 (m, 16 H), 8.14–8.17 (m, 2H).

EXAMPLE 11

Synthesis of 5β, 20-epoxy-1,2α,4,7β,10β,13α-hexahydroxytax-11-en-9-one 4,10-diacetate 2-benzoate 13-ester with (2R,3S)-N-methacryoyl-3-phenylisoserine The procedure is similar to the procedure for synthesis of 5β, 20-epoxy-1,2α,4,7β,10β,13α-hexahydroxytax- 11-en-9-one 4,10-diacetate 2-benzoate 13-ester with (2R,3S)-N-α-methylcinnamoyl-3-phenylisoserine by using methacrylic acid instead of α-methylcinnamic acid.
$^1$H NMR (400 MHz, $CD_3COCD_3$) δ: 1.21 (s, 3H), 1.25 (s, 3H), 1.69 (s, 3H), 1.75–1.83 (m, 1H), 1.93 (s, 3H), 1.97 (s, 3H), 2.10–2.24 (m, 1H), 2.33 (s, 3H), 2.34–2.52 (m, 2H), 2.42 (s, 3H), 3.50 (d, J=6.0 Hz, 1H), 3.85–3.88 (m, 2H), 4.18 (q, J=8.3 Hz, 2H), 4.43 (pentet, J=5.6 Hz, 1H), 4.81 (dd, J=6.4, 4.4 Hz, 1H), 4.95 (dd, J=9.2, 4.0 Hz, 1H), 5.06 (d, J=7.2 Hz, 1H), 5.38 (s, 1H), 5.62 (dd, J=8.8, 4.4 Hz, 1H), 5.71 (J=7.2 Hz, 1H), 5.78 (s, 1H), 6.22 (t, J=9.0 Hz, 1H), 6.43 (s, 1H), 7.12–7.72 (m, 9H), 8.14 (d, J=8.0 Hz, 2H).

EXAMPLE 12

Synthesis of 5β, 20-epoxy-1,2α,4,7β,10β,13α-hexahydroxytax-11-en-9-one 4,10-diacetate 2-benzoate 13-ester with (2R,3S)-N-α-methylcinnamoyl-O-benzoyl-3-phenylisoserine (Compound 8)

Compound 7 from the above procedure was added with 1L of methylene chloride, 9.5 g of triethylamine and 4 g of benzoylchloride at ice temperature. After stirring for 3 h, 110 mL of methanol was added and this mixture was stirred for another 2 h. Washing the solution with water and brine, drying over $MgSO_4$ and removing solvent under reduced pressure gave crude Compound 8. Crystallization of this crude product by methanol gave purified 30 g of Compound 8 (60% yield from Compound 4 to 8).
$^1$H NMR (400 MHz, $CD_3COCD_3$) δ: 1.20 (s, 3H), 1.22 (s, 3H), 1.68 (s, 3H), 1.75–1.85 (m, 1H), 2.04 (s, 3H), 2.09 (s, 3H), 2.07–2.10 (m, 1H), 2.17 (s, 3H), 2.37 (dd, J=15.4, 9.5 Hz, 2H), 2.50 (s, 3H), 2.46–2.53 (m, 1H), 3.63 (d, J=5.9 Hz, 1H), 3.88 (d, J=7.1 Hz, 1H), 3.95 (s, 1H), 4.17 (d, J=8.1 Hz, 1H), 4.20 (d, J=8.1 Hz, 1H), 4.46 (m, 1H), 4.99 (d, 7.7 Hz, 1H), 5.70 (d, J=7.2 Hz, 1H), 5.73 (d, J=6.1 Hz, 1H), 6.06–6.10 (m, 1H), 6.21, (t, J=8.5, 1H), 6.45 (s, 1H), 7.28–7.71 (m, 16 H), 8.12–8.15 (m, 4H), 8.35 (d, J=8.5 Hz, 1H).
$^{13}$C NMR (100 MHz, $CD_3COCD_3$) δ: 9.7, 14.4, 14.7, 20.3, 22.7, 26.6, 43.7, 46.7, 54.0, 58.5, 72.1, 75.4, 75.7, 76.0, 78.3, 81.2, 128.0, 128.2, 128.7, 128.8, 129.0, 129.1, 129.2, 129.4, 129.7, 130.2, 130.4, 130.8, 133.2, 133.4, 133.6, 133.9, 134.2, 136.5, 138.1, 141.8, 165.9, 166.1, 169.2, 170.1, 170.2, 170.4, 203.3.

EXAMPLE 13

Synthesis of 5β, 20-epoxy-1,2α,4,7β,10β,13α-hexahydroxytax-11-en-9-one 4,10-diacetate 2-benzoate 13-ester with (2R,3S)-N-pyruvoyl-O-benzoyl-3-phenylisoserine (Compound 9)

Compound 8 (4.36 g) was dissolved in methylene chloride (150 ml) in a 3-necked 1L round bottom flask equipped with a stirring bar, thermometer and two glass tubes (inlet and outlet for $O_3$). The flask was immersed in a cooling bath (acetone dry ice) which was rested on a magnetic stirrer. When the temperature of the solution reached −50° C. ozone was passed through the mixture for 4 minutes. Subsequently the reaction mixture was dropwise treated with 1 ml of dimethylsulfide. Removal of the solvent on rotavap gave a crude residue Compound 9. The crude Compound 9 was purified by chromatography on silica gel with acetone and hexane to provide purified Compound 9 (3.96g).
$^1$H NMR (400 MHz, $CD_3COCD_3$) δ: 1.17 (s, 3H), 1.18 (s, 3H), 1.65 (s, 3H), 1.68–1.86 (m, 1H), 1.96 (s, 3H), 2.15 (s, 3H), 2.12–2.24 (m, 1H), 2.33–2.47 (m, 2H), 2.37 (s, 3H), 2.42 (s, 3H), 3.48 (d, J=6.0 Hz, 1H), 3.76 (s, 1H), 3.81 (d, J=7.2 Hz, 1H), 4.15 (dd, J=13.8, 8.2 Hz, 2H), 4.43 (pentet, J=5.2 Hz, 1H), 4.95 (d, J=8.8 Hz, 1H), 5.66 (d, J=7.2 Hz, 1H), 5.72–5.80 (m 2H), 6.10 (t, J=9.2 Hz, 1H), 6.42 (s, 1H), 7.29 (t, J=7.4 Hz, 1H), 7.46–7.73 (m, 10H), 8.09 (t, J=8.4 Hz, 4H), 8.72 (br, 1H).
$^{13}$C NMR (100 MHz, $CD_3COCD_3$) δ: 9.7, 14.4, 20.3, 22.7, 24.3, 26.6, 36.1, 36.3, 43.6, 46.2, 54.6, 58.5, 71.4, 71.5, 75.7, 75.8, 75.6, 78.3, 81.1, 84.5, 128.2, 128.8, 129.2, 129.3, 129.4, 129.9, 130.1, 130.4, 130.8, 133.7, 134.0, 134.3, 137.0, 141.7, 161.0, 165.7, 166.1, 169.2, 170.2, 170.4, 196.5, 203.2.

EXAMPLE 14

Synthesis of 5β, 20-epoxy-1,2α,4,7β,10β,13α-hexahydroxytax- 11-en-9-one 4,10-diacetate 2-benzoate 13-ester with (2R,3S)-N-pyruvoyl-O-benzoyl-3-phenylisoserine (Paclitaxel)

543 mg of Compound 9 and 211 mg of o-phenylenediamine was dissolved in 25 mL THF. 1.98 g of acetic acid was added to the THF solution at room temp and then the reaction flask was placed in a 45° C. oil bath. After 30 hours, the solvent was removed under reduced pressure. 20 mL of MeOH, 80 ml $H_2O$ and 20 mL 1N HCl were added to the residue and stirred for 10 minutes to give a precipitate. Filtration through filter paper gave 445 mg of the taxol product.
$^1$H NMR (400 MHz, $CD_3COCD_3$) δ: 1.20 (s, 3H), 1.22 (s, 3H), 1.69 (s, 3H), 1.76–1.83 (m, 1H), 1.93 (s, 3H), 2.17 (s, 3H), 2.22 (dd, J=15.4, 9.1 Hz, 1 H), 2.41 (dd, J=15.4, 9.1 Hz, 1 H), 2.44 (s, 3H), 2.44–2.52 (m, 1H), 3.57 (d, J=5.8 Hz, 1H), 3.87 (d, J=7.1 Hz, 1H), 3.95 (s, 1H), 4.17 (d, J=8.1 Hz, 1H), 4.20 (d, J=8.2 Hz, 1H), 4.38–4.45 (m, 1H), 4.87 (dd, J=7.1, 4.8 Hz, 1H), 4.98 (d, J=9.5 Hz, 1H), 5.22 (d, J=7.1 Hz, 1H), 5.70 (d, J=7.1 Hz, 1H), 5.78 (dd, J=8.8, 4.6 Hz, 1H), 6.21 (t, J=8 Hz, 1H), 6.42 (s, 1H), 7.31 (t, J=7.2 Hz, 1H), 7.41–7.70 (m, 10H), 7.91–7.93 (m, 2H), 8.11–8.15 (m, 3H).
$^{13}$C NMR (100 MHz, $CD_3COCD_3$) δ: 9.7, 14.3, 20.3, 21.9, 22.6, 26.6, 36.3, 36.7, 43.7, 46.7, 56.5, 58.6, 71.4, 71.9, 74.3, 75.4, 75.7, 76.3, 78.3, 81.2, 84.5, 127.8, 127.9, 128.0, 128.7, 128.8, 129.0, 130.4, 130.8, 131.8, 133.6, 133.9, 139.8, 141.5, 166.1, 167.2, 170.2, 170.6, 173.2, 203.3.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method for synthesizing taxane derivatives comprising the steps of coupling an oxazole intermediate of the general formula:

(4)
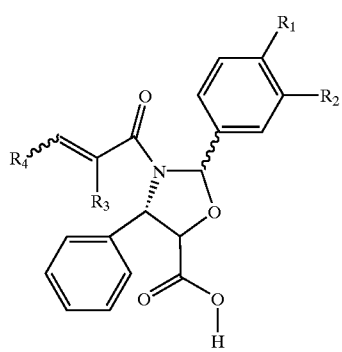

in which $R_1$ is —O-alkyl, $R_2$ is —O-alkyl or hydrogen, $R_3$ is lower alkyl and $R_4$ is alkyl or aryl, with a baccatin III derivative (5) that is protected at the C-7 position by a protecting group X to produce compound (6)

(5)
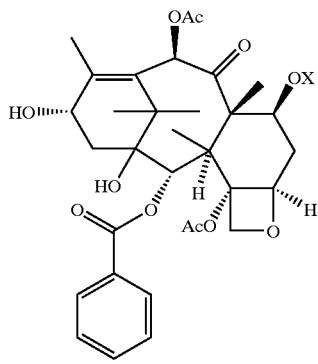

(6)
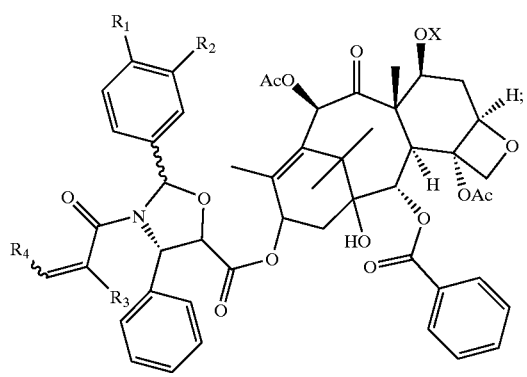

removing the protecting group X and oxazole group to produce compound (7)

(7)
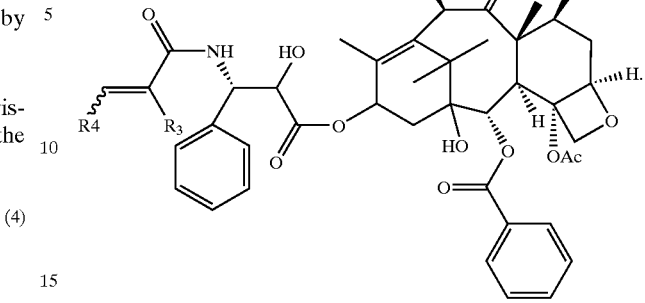

2. The method of claim 1 wherein $R_3$ is methyl and X is triethylsilyl.

3. The method of claim 1 wherein $R_3$ is methyl, $R_4$ is phenyl and X is triethylsilyl.

4. The method of claim 1 wherein the compound 7 is reacted with a carboxylic acid or derivative to form compound of structure 8 in which $R_6$ is alkyl-O, alkyl, alkenyl or (8)
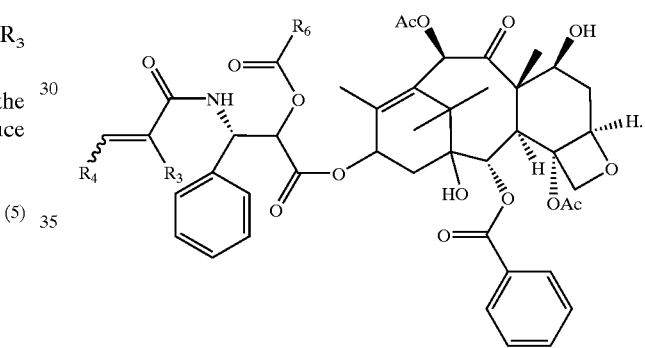

5. The method of claim 4 where compound 8 is reacted with ozone and phenylene diamine to produce a taxane derivative 10

(10)
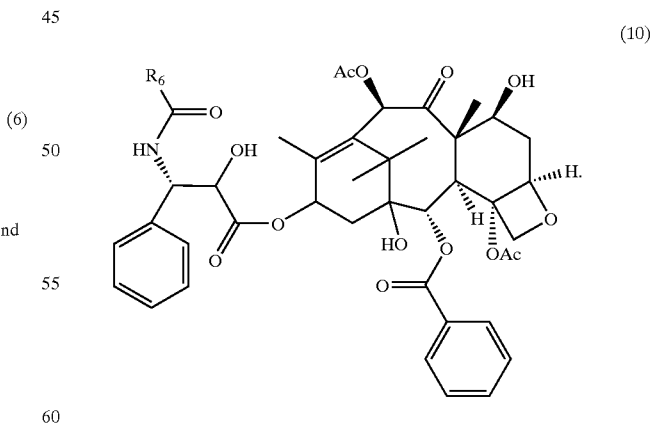

6. The method of claim 4 wherein $R_6$ is aryl, $R_3$ is methyl and $R_4$ is lower alkyl or phenyl.

7. The method of claim 6 wherein $R_6$ is phenyl.

8. THe method of claim 4 wherein $R_6$ is t-butoxide.

9. A compound of structure (4) wherein $R_1$ is —O-alkyl, $R_2$ is —O-alkyl or hydrogen, $R_3$ is lower alkyl, and $R_4$ is alkyl or aryl (4)

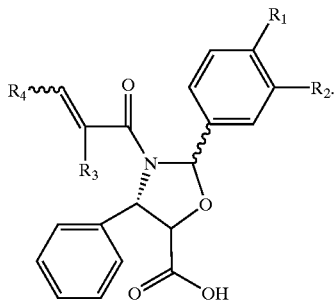

10. The compound according to claim 9 where $R_1$ is —OMe, $R_2$ is —OMe or hydrogen, and $R_3$ is methyl.

11. A compound of structure (6) wherein $R_2$ is —O-alkyl, $R_2$ is —O-alkyl or hydrogen, $R_3$ is lower alkyl, and $R_4$ is alkyl or aryl (6)

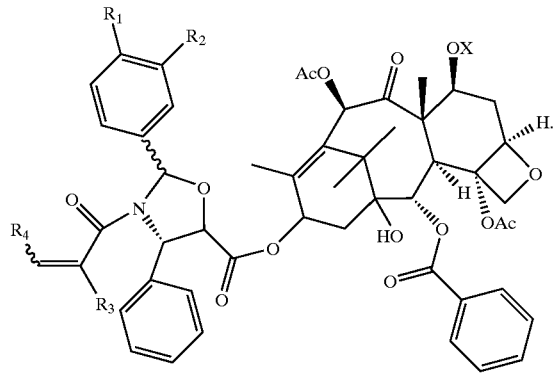

12. The compound of claim 11 wherein the protecting group X is trialkyl silyl and $R_3$ is methyl.

13. The compound of claim 11 wherein $R_1$ is —OMe, $R_2$ is —OMe or hydrogen, $R_3$ is methyl, $R_4$ is phenyl, and X is triethylsilyl.

14. A compound of structure (7) wherein $R_3$ is methyl and $R_4$ is aryl (7)

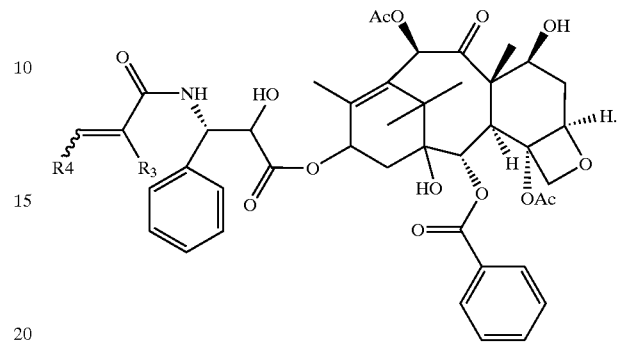

15. A compound of structure (8) where $R_3$ is methyl, $R_4$ is aryl, and $R_6$ is alkyl, aryl or alkoxide (8)

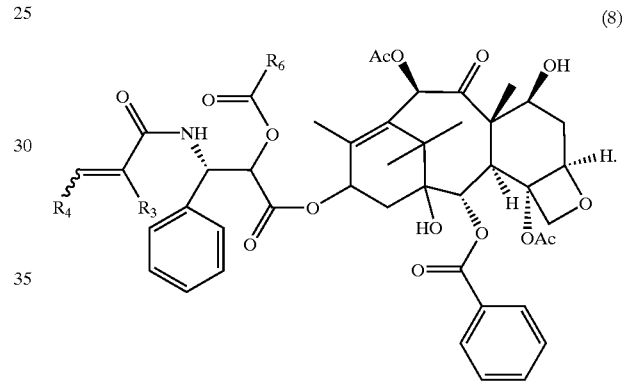

* * * * *

UNITED STATES PATENT AND TRADEMARK OFFICE
CERTIFICATE OF CORRECTION

PATENT NO. : 6,531,611 B2  
DATED : March 11, 2003  
INVENTOR(S) : George Schloemer et al.

It is certified that error appears in the above-identified patent and that said Letters Patent is hereby corrected as shown below:

<u>Title page,</u>
Item [75], change inventor's name from "Chien Hsin Lin" to read
-- Chien Hsing Lin --.
Item [73], change assignee name from "Scinopharm Taiwan, Ltd., Tainan (TW)"
to read -- ScinoPharm Taiwan, Ltd. Tainan (TW) --.

Signed and Sealed this

Twelfth Day of August, 2003

JAMES E. ROGAN
*Director of the United States Patent and Trademark Office*